United States Patent [19]

Aggarwal et al.

[11] Patent Number: 5,650,316

[45] Date of Patent: Jul. 22, 1997

[54] USES OF TRIPLEX FORMING OLIGONUCLEOTIDES FOR THE TREATMENT OF HUMAN DISEASES

[75] Inventors: Bharat B. Aggarwal, Houston; Robert F. Rando; Michael E. Hogan, both of The Woodlands, all of Tex.

[73] Assignee: Research Development Foundation, Carson City, Nev.

[21] Appl. No.: 254,114

[22] Filed: Jun. 6, 1994

[51] Int. Cl.$^6$ .............................. C12N 5/10; C07H 21/04; C12Q 1/68; G01N 33/574

[52] U.S. Cl. .............................. 435/375; 435/6; 435/7.23; 514/44; 536/24.5; 536/24.31; 536/24.32; 536/24.33

[58] Field of Search .............................. 514/44; 536/24.5, 536/24.31, 24.32, 24.33; 435/240.2, 6, 7.23; 935/6, 8, 33, 34, 36

[56] References Cited

PUBLICATIONS

L. Guarini et al., Int. J. Cancer, vol. 46 ('90) pp. 1041–1047.
Y. De Guchi et al., Clin. Exp. Immunol., vol. 85 ('91) pp. 392–395.
R. Williams et al., PNAS, vol. 89 ('92) pp. 9784–9788.
K. Selmaj et al, Annals Neurol., vol. 30 ('91) pp. 694–700.
A. Hansen et al. [Abstract] Virchows Arch. B. Cell Pathol. Incl. Mol. Pathol., vol. 63(2) ('93) pp. 107–113.
R. Weiss, Science News, vol. 139 ('91) pp. 108–109.
E. Uhlmann et al, Chemical Reviews, vol. 90(4) ('90) pp. 543–584.
L. Kibler–Herzog et al., Nucl. Acids Res., vol. 18(12) ('90) pp. 3545–3555.
Y.–K. Cheng et al., Prog. Biophys. Mol. Biol., vol. 58 ('92) pp. 225–227.
L. Stein et al., Science, vol. 261 ('93) pp. 1004–1012.
L.J. Maher et al., BioEssays, vol. 14(12) ('92) pp. 807–815.
W. McShan et al., JBC, vol. 267(8) ('92) pp. 5712–5721.
A. Shakov et al., J. Exp. Med., vol. 171 ('90) pp. 35–47.

*Primary Examiner*—Charles C. P. Rories
*Attorney, Agent, or Firm*—Benjamin Aaron Adler

[57] ABSTRACT

The present invention provides novel methods of treating anti-neoplastic and non-neoplastic cell proliferative diseases. The present methods involve administration of triplex forming oligonucleotides to humans to inhibit the biological activity of tumor necrosis factor. Also provided are methods of treating neuro-oncologic states and renal cancer.

4 Claims, 16 Drawing Sheets

SEQUENCE LISTING ( 1 ) GENERAL INFORMATION:

( i i i ) NUMBER OF SEQUENCES:4

( 2 ) INFORMATION FOR SEQ ID NO: 1:

( i ) SEQUENCE CHARACTERISTICS:
        ( A ) LENGTH: 29 base pairs
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:1:

GGGGTGTGTG TGGGGTTGGT GGGTTGTGG                29

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:2:

GTGTGGTGTG GGTGTGTGGG TGGGTGG                  27

( 2 ) INFORMATION FOR SEQ ID NO: 3:

( i ) SEQUENCE CHARACTERISTICS:
        ( A ) LENGTH: 26 base pairs
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: no ( i v ) ANTI-SENSE: no ( v ) SEQUENCE DESCRIPTION: SEQ ID NO:3:

TTGTTTGGGG TGGGTGGTGT GTGGGG                   26

( 2 ) INFORMATION FOR SEQ ID NO: 4:

( i ) SEQUENCE CHARACTERISTICS:
        ( A ) LENGTH: 26 base pairs
        ( B ) TYPE: nucleic acid
        ( C ) STRANDEDNESS: double- stranded
        ( D ) TOPOLOGY: linear ( i i ) MOLECULE TYPE: DNA ( i i i ) HYPOTHETICAL: no -continued ( i v ) ANTI-SENSE: no ( i x ) FEATURE:
    ( D ) OTHER INFORMATION: N is 5- fluorodeoxyuracil ( x i ) SEQUENCE DESCRIPTION: SEQ ID NO:4:

TTGTTTGGGG    NGGGTGGTGT    GNGGGG    26

USES OF TRIPLEX FORMING OLIGONUCLEOTIDES FOR THE TREATMENT OF HUMAN DISEASES

BACKGROUND OF THE INVENTION

1. Field of the Invention

The present invention relates generally to the fields of molecular genetics and pharmacology. More specifically, the present invention relates to novel triplex forming oligonucleotides for the treatment of human diseases.

2. Description of the Related Art

It is now generally accepted that a pathological situation is a result of deregulation or overexpression of certain cellular genes. During the last few years a great deal of insight has been gained into the mechanism by which cellular genes perform their function. It is this understanding which has led to the use of specific synthetic oligodeoxynucleotides to inactivate particular cellular genes in an attempt to correct certain abnormalities in the cell. Oligodeoxynucleotides that can interact with specific cellular mRNA and inhibit the activity or expression of its product has been in use for last several years. Oligodeoxynucleotides have also been described which bind specific proteins and inhibit their activity.

Recently, oligodeoxynucleotides have been described which inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are generally called triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor.

Tumor necrosis factor (TNF), a protein with a molecular mass of 17 kDa, was originally described as a product of activated macrophages and shown to display tumoricidal activity. Extensive research during the last few years has made it apparent that TNF is a highly pleiotropic cytokine and may play a role in tumorigenesis, septic shock, cachexia, inflammation, autoimmunity and other immunological and pathological reactions. Several different type of tumors have been described in which TNF acts as an autocrine growth factor, including different type of leukemias, ovarian tumors, renal cell carcinoma, breast adenocarcinoma and glioblastoma. These tumors express both TNF and its receptors and, furthermore, these tumors proliferate in response to TNF.

The prior art remains deficient in the absence of effective pharmacological therapies for a wide variety of neoplastic conditions. The present invention fulfills this longstanding need and desire in the art.

SUMMARY OF THE INVENTION

In one embodiment of the present invention, there is provided a method of treating a pathophysiological state characterized by an undesirable physiological level of tumor necrosis factor comprising the step of administering a pharmacologically effective dose of a triplex forming oligonucleotide to a human, said dose being sufficient to inhibit the transcription of the gene coding for tumor necrosis factor.

In another embodiment of the present invention, there is provided a method of inhibiting the production of tumor necrosis factor in an individual having a neoplastic disease comprising the step of administering a pharmacological dose of a triplex forming oligonucleotide to a human, said dose being sufficient to inhibit the transcription of the gene coding for tumor necrosis factor.

In yet another embodiment of the present invention, there is provided a method of treating a neuro-oncologic state comprising administering to a human a pharmacological dose of a triplex forming oligonucleotide, said dose being sufficient to inhibit the transcription of the gene coding for tumor necrosis factor.

In still yet another embodiment of the present invention, there is provided a method of treating renal cancer comprising administering to a human a pharmacologically effective dose of a triplex forming oligonucleotide, said dose being sufficient to inhibit the transcription of the gene coding for tumor necrosis factor.

Other and further objects, features and advantages will be apparent from the following description of the presently preferred embodiments of the invention given for the purpose of disclosure when taken in conjunction with the accompanying drawings.

BRIEF DESCRIPTION OF THE DRAWINGS

The following figures are provided to illustrate various aspects of the present invention. To that end, some of the figures are presented in schematic form and are not necessarily drawn to scale.

DETAILED DESCRIPTION OF THE INVENTION

Figure 1:
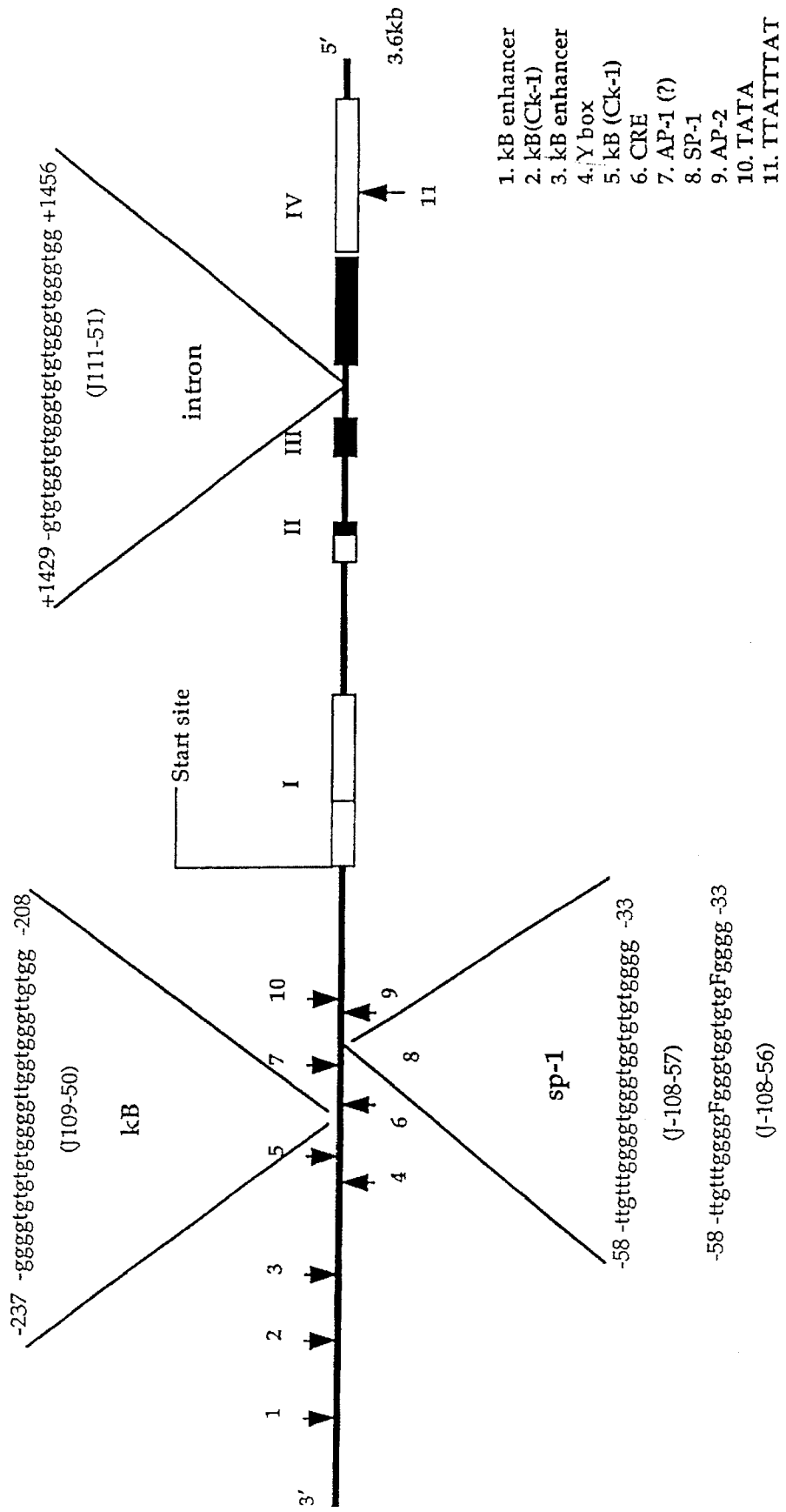
FIG. 1 shows the sequence and design of different oligodeoxynucleotides directed to different regions of the TNF gene.

It is readily apparent to one skilled in the art that various substitutions and modifications may be made to the invention disclosed herein without departing from the scope and spirit of the invention.

As used herein, the term "TFO" or "triplex forming oligonucleotide" refers to the synthetic oligonucleotides of the present invention which are capable of forming a triple helix by binding in the major groove with a duplex DNA structure. U.S. Pat. No. 5,176,996, issued on January 5, 1993 to Hogan & Kessler discloses methods for making triplex forming oligonucleotides.

As used herein, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods of the present invention.

As used herein, the term "inhibition" of cell proliferation is meant to include partial and total inhibition of cell proliferation as well as decreases in the rate of cell growth, i.e., both cytotoxic and cytostatic effects. The inhibitory dose or "therapeutic dose" of the compounds of the present invention may be determined by assessing the effects of the TFO on tumor cell proliferation in tissue culture or on tumor growth in an art-accepted animal model. The amount of the TFO administered in a therapeutic context is dependent, inter alia, upon the age, weight, kind of concurrent treatment and nature of the neoplastic condition being treated.

As used herein, the term "pharmacological dose" refers to the dose of a TFO which causes a pharmacological effect when given to a mammal. The pharmacological dose introduced will provide a sufficient quantity of TFO to induce a specific and measurable effect, e.g., (1) cytoxicity, (2) cytostasis, (3) damaging the duplex DNA at the target site or (4) inhibiting the transcription/translation of the TNF gene. Given the parameters discussed above, one skilled in this art would readily determine the appropriate pharmacological dose.

Synthetic oligodeoxyribonucleotides which inhibit the expression of specific genes is becoming a novel means of controlling the activity of a gene. Oligonucleotides which bind double stranded DNA by formation of triple helices have advantages over therapies which bind the gene product, i.e., mRNA (antisense technology). In the present invention, the effects of different triple helix forming oligodeoxynucleotides (TFOs) on production of tumor necrosis factor (TNF) and on cellular growth of various tumors in which TNF acts as an autocrine growth factor are shown. The oligonucleotides, J-109-50 and J-108-56 were designed to interact with nuclear factors kB binding sites (−237 to −208) and Sp1 binding sites (−58 to −33), respectively. The TFO J111-51 was designed to interact with the third intron surrounded by the coding region (+1429− to +1456) of the TNF gene. A person having ordinary skill in this art would readily appreciate that the gene sequence of tumor necrosis factor is well known in the art. In order-to enhance the cellular penetration and prevent the degradation by cellular nucleases, TFOs were modified at their 3' end by either a cholesterol side chain or an amino blocking group.

TABLE I provides detailed information on the synthesis of the different triplex forming oligonucleotides useful in the methods of the present invention.

TABLE I

| TFO | [μM] | Modification | Gene Target |
| --- | --- | --- | --- |
| J108-56 | | cholesterol Flurodeoxyuracil | TNF(SP-1; −58 to −33) |
| J108-57 | | cholesterol | TNF(SP-1; −58 to −33) |
| J109-50 | | amine | TNF (kB; −237 to −208) |
| J111-51 | | cholesterol | TNF(intron-3; +1429 to +1456) |
| J100-11 | 630 | phosphorothioate | 45mer random mix |
| J111-01 | 730 | cholesterol | reverse orientation of J111-51 |
| J111-56 | 990 | cholesterol | scramble sequence of J111-51 |
| B106-96 | | phosphorothioate | G-rich TFO |
| 1208 | | phosphorothioate | random |
| J109-51 | | cholesterol | TNF (NF-kB); −237 to −238 |

Treatment of human promonocytic cell line, THP-1 with TNF-TFOs at a concentration not toxic to cells (2 μM) reduced the production of TNF by greater than 80%. All TNF-TFOs examined were effective and control TFOs (designed against Herpes) were ineffective in inhibiting TNF production. Among the TNF-TFOs, J111-51 designed to interact with the third intron was found to be maximally effective. In the human glioblastoma tumor cell line, U-251, TNF acts an autocrine growth factor and this activity of TNF is blocked by J111-51 in a dose-dependent manner. Thus, oligonucleotides directed to the specific regions of TNF useful in cancer and septic shock therapy.

Thus, the present invention provides a method of treating a pathophysiological state characterized by an undesirable physiological level of tumor necrosis factor comprising the step of administering a pharmacological dose of a triplex forming oligonucleotide to a human, said dose being sufficient to inhibit the transcription of the gene coding for tumor necrosis factor.

The present invention also provides a method of inhibiting the production of tumor necrosis factor in a human having a neoplastic disease comprising the step of administering a pharmacological dose of a triplex forming oligonucleotide, said dose being sufficient to inhibit the transcription of the gene coding for tumor necrosis factor.

Generally, the TFOs useful in the methods of the present invention may be any that specifically disrupt transcription of TNF. Most preferably, the TFO has a sequence appropriate to bind to the preferred target regions of the TNF gene as listed in TABLE I.

Generally, the pathophysiological state treated by the methods of the present invention is any state in which inhibition of tumor necrosis factor is desirable. Accordingly, the pathophysiological states treated may be ones in which the physiological concentrations of TNF are undesirably high. Alternatively, the methods of the present invention may be used to treat pathophysiological state where the level of TNF is "normal" but a reduction in physiological levels of TNF may be therapeutically desirable.

Thus, the methods of the present invention may be used to treat such conditions as neoplastic diseases, the human immunodeficiency disease, sepsis, cachexia, graft vs host disease, autoimmune diseases cerebral malaria and capillary leak syndrome. Representative examples of neoplastic diseases include leukemias, ovarian carcinoma, renal cell carcinoma, breast adenocarcinoma and glioblastoma. Representative examples-of autoimmune diseases include systemic lupus erythematosus, rheumatoid arthritis and multiple sclerosis.

In another embodiment, the present invention is directed to a method of treating a neuro-oncologic state, comprising administering to a human a pharmacologically effective dose of a triplex forming oligonucleotide, said dose being sufficient to inhibit the transcription of the gene coding for tumor necrosis factor. Preferably, the neuro-oncologic state is glioblastoma, an astrocytoma or a meningioma. It is also specifically contemplated that advantageous and therapeutically more efficacious effects may be seen when more than one triplex forming oligonucleotide is administered concurrently. That is, the present invention provides a method of treating a neuro-oncologic state, wherein two triplex forming oligonucleotides directed against different target sites within the TNF gene are administered concomitantly. Alternately, three triplex forming oligonucleotides having different target sites within the TNF gene are administered concomitantly.

Also provided by the present invention is a method of treating renal cancer comprising administering to a human a pharmacologically effective dose of a triplex forming oligonucleotide, said dose being sufficient to inhibit the transcription of the gene coding for tumor necrosis factor.

The following examples are provide solely for the purpose of illustrating various embodiments of the present invention and are not meant to limit the present invention in any fashion.

EXAMPLE 1

Chemicals

Highly purified, bacteria-derived recombinant human TNF with a specific activity of $5.0 \times 10^6$ units/mg was provided by Genentech, Inc. (South San Francisco, Calif.). Dulbecco's modified Eagle's medium (DMEM/F12) was obtained from ICN Biomedical Corp. (Irvine, Calif. ), RPMI-1640 and EMEM was from Whittaker, Mass. Bio-products (Walkersville, Md.); fetal bovine serum (FBS) and gentamicin was from GIBCO (Grand Island, N.Y.). Carrier-free $Na^{125}I$ was purchased from Amersham (Arlington Heights, Ill.); PD-10 (prepacked Sephadex G-25 Medium) columns were obtained from Pharmacia Fine Chemicals (Piscataway, N.J.); actinomycin D, cycloheximide, iodogen, protein A-Sepharose, bovine serum albumin (BSA), and gelatin were from Sigma Chemical Co. (St. Louis, Mo.). Suramin was obtained from Miles Inc. (West Haven, Conn.). Polystyrene 12-well flat bottom tissue culture corning plates (#25815) were obtained from VWR Scientific; (Houston, Tex.); and flexible 96-well round-bottom assay plates were from Becton Dickinson and Co. (Oxnard, Calif.; Lincoln Park, N.J.).

EXAMPLE 2

Design and Synthesis of Oligodeoxynucleotides

All oligodeoxynucleotides were synthesized on an Applied Biosystems Inc. (ABI) DNA synthesizer model 380B or 394, using standard phosphoramidite methods at 0.2 or 1.0 µg mole scales. 5'-protected nucleoside phosphoramidite monomers and other reagents were obtained from Milligen with the exception of acetonitrile, which was obtained from Baxter. All oligonucleotides were synthesized with a 3'-Amino Modifier (Glen Research), which results in the covalent attachment of a propanolamine group to the 3'-hydroxyl group (as described by Durland, et al., Binding of Triple Helix Forming Oligonucleotides to Sites in Gene Promoters, Biochem. 1991; 30:9246–9255 and Nelson, et al., Bifunctional oligonucleotide probes synthesized using a novel CPG support are able to detect single base pair mutations, Nucleic Acids Res. 1989; 17:7187–7191) or with a cholesterol moiety attached to the 3'-end via a tri-glycyl linker as described by Vu, et al., Synthesis of Cholesteryl Supports and Phosphoramidites Containing a Novel Peptidyl Linker for Automated Synthesis of Triple-Helix Forming Oligonucleotides and Uses Thereof, in Second International (20th) Symposium on Nucleic Acids Chemistry. 1993, Nucleic Acids Research Symposium, Sapporo, Japan. Phosphorothioate containing oligonucleotides were prepared using the sulfurizing agent TETD as described by Vu and Hirschbein, Tetrahedron Letters 332:3005–8 (1991). The purity of the oligonucleotide was confirmed by analytical HPLC, electrophoresis of $^{32}$P-labeled oligonucleotide on a 20% polyacrylamide gel containing 7M urea and by capillary gel electrophoresis. The 3'-cholesteryl modified oligonucleotides were prepared and purified as described by Vu et al.

FIG. 1 shows the design of three different type of TFOs. One TFO was a 29 mer directed to the kB site in the promoter region of the TNF gene (−237 to −208) and is referred to as J109-50. A second and third TFO was a 26mer directed to sp1 site in the TNF promoter region (−58 to −33) and is referred to as either J108-57 and J108-56 (differing only in modification at two positions from thymine to 5-florodeoxyuracil). A fourth TFO was a 27mer directed to a region in the third intron (+1429 to +1456) and referred to as J111-51. The TFO referred to as B106-96 was a 36mer with phosphorothioate backbone designed against Herpes virus and was used as nonspecific control. Another TFO, 1208 was also a nonspecific 36mer purine rich control.

EXAMPLE 3

Cells

The mouse connective tissue cell line L-929 (CCL 1) and human promonocytic cell line THP-1 were obtained from American Type Culture Collection, (Rockville, Md.). The U-251 cell line, human glioblastoma cells, were provided by Dr. J. S. Rao of the M.D. Anderson Cancer Center, Houston, Tex. L-929, THP-1 and U-251 cells were routinely grown in EMEM, RPMI-1640 and DMEM/F12 media respectively supplemented with glutamine (1%), gentamicin (50 μg/ml), and FBS (10%) in a humidified incubator in 5% $CO_2$ in air. Cells were tested for mycoplasma contamination using a DNA-based assay kit purchased from Gen-Probe (San Diego, Calif.). Murine L-929 cell cultures were maintained in continuous exponential growth by twice a week passage.

EXAMPLE 4

TNF Bioassays

The TNF bioassay was carried out with $2.0 \times 10^4$ L-929 cells treated with actinomycin D (1 μg/ml) along with TNF for 24 hours. For this, cells were plated for overnight in 0.1 ml of the medium (EMEM-1640 with 10% FBS) in 96-well Falcon plates. Thereafter, the medium was removed and a serial dilution of human TNF was layered in 0.1 ml of the volume. After 24 hours of incubation at 37° C., the medium was removed and viable cells were monitored by crystal violet staining according to the procedure described by Sugarman et al., Recombinant human tumor necrosis factor-alpha: Effects on proliferation of normal and transformed cells in vitro. *Science*, 230:943–945 (1985). It was determined that the dye uptake method to examine cell viability correlates with cell number determined by detachment with a trypsin solution and microscopic counting with hemocytometer. The percentage of relative cell viability was calculated as optical density in the presence of the test sample divided by optical density in the absence of the test sample (medium) multiplied by 100.

EXAMPLE 5

Cell Proliferation Assays

Cell growth stimulation assays were carried out essentially according to the procedure described by Hudziak et al., Amplified expression of the HER2/erbB2 oncogene induces resistance to tumor necrosis factor-alpha in NIH 3T3 cells. *Proceedings of the National Academy of Science, USA*, 85(14):5102–5106, 1988. Briefly, to determine the effect of human TNF, cells ($5 \times 10^3$/well) were plated in 0.2 ml of the medium (DMEM/F12 plus 10% FBS) in 96-well corning plates. After overnight incubation in a $CO_2$ incubator at 37° C., the medium was removed and test sample was layered in 0.2 ml of the fresh medium. After different days of incubation, the medium was decanted and cells were counted by hemocytometer. All determinations were made in triplicate. For [$^3$H] TdR incorporation assays, cells were cultured and treated with TNF the same as indicated above for 3 days. During the last 6 hours, [$^3$H] TdR (6.7 Ci/mmole) was added to each well (0.5 μCi/well). Thereafter, the culture medium was removed, the wells were washed twice with phosphate-buffered saline (PBS) and the cells were detached by the addition of a solution of trypsin (0.5%) with EDTA (5.3 mM). The cell suspension was then harvested with the aid of a Filtermate 196 cell harvester (Packard Instruments, Canberra, Australia) and lysed by washing with distilled water. Radioactivity bound to the filter was measured directly by Direct Beta Counter Matrix 9600 (Model 1600 TR; Packard Co., Meriden, Conn.). Thymidine incorporation in human fibroblasts determined by this method has been shown to correlate with cell growth.

EXAMPLE 6

Radioreceptor Assay

Receptor binding assays were carried out essentially as described previously by Aggarwal et al., Characterization of receptors for human tumor necrosis factor and their regulation by gamma-interferon. *Nature*, 318(6047):665–667, 1985. TNF-a was labeled with $Na^{125}I$ using the Iodogen method. The specific activity of the labeled TNF-a ranged from 20–30 mCi/mg. Standard binding assays were performed in flexible 96-well plates precoated with 0.2 ml of FBS for 24 hours at 4° C. The binding medium (DMEM/F12) contained 10% FBS. Cells ($1 \times 10^6$/0.1 ml) were incubated with increasing amounts of $^{125}I$-TNF-a in the absence (total binding) or in the presence of 100 nM unlabeled ligand (nonspecific binding) for 1 hour at 4° C. The cells were washed three times with ice-cold medium (PBS containing 0.1% BSA) at 4° C., and the cell-bound radioactivity was determined in a gamma-counter. Each determination was performed in triplicate. Specific binding of the $^{125}$-I labeled TNF-α was calculated by subtraction of nonspecific binding from the total binding.

EXAMPLE 7

TNF-TFOs Inhibit Cellular Production of TNF

Figure 2:
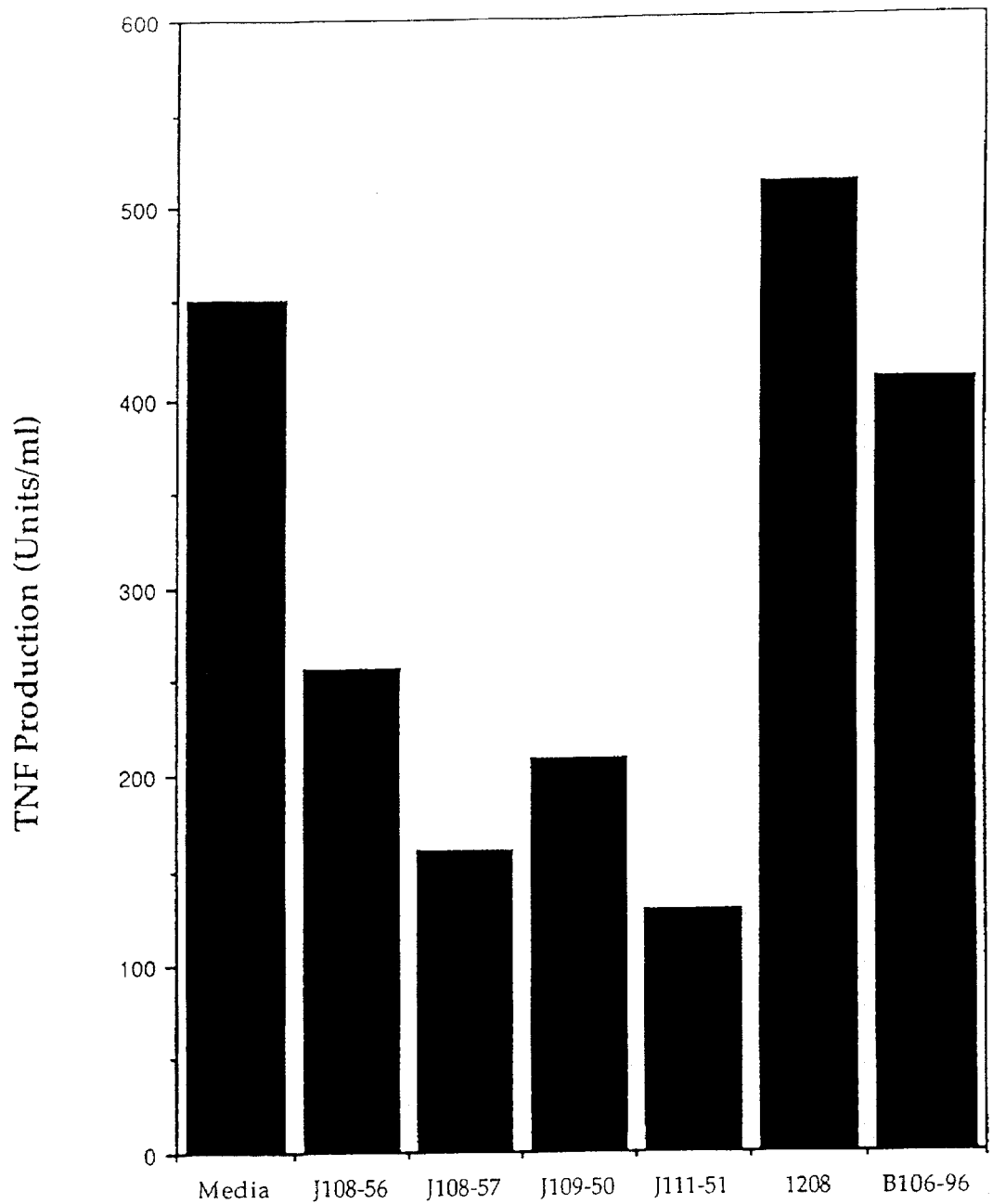
FIG. 2 shows the effect of TNF-TFOs on the production of TNF from human promonocytic cell line, THP-1. $1\times10^6$ cells (1 ml) in 12-well plates were incubated for 72 hours in the presence of PMA (100 ng/ml) and TFOs (J108-56, J108-57, J109-50 and J111-51 were 2 µM whereas 1208 and B106-96 were 0.5 uM) at 37° C. Thereafter, the cell supernatants were harvested and assayed in triplicate for activity in L-929 bioassay for TNF.

The effect of various TFOs on the production of TNF from human promonocytic THP-1 cells activated with phorbol esters was examined. FIG. 2 illustrates that the treatment of cells with phorbol ester (100 ng/ml) for 72 hours leads to production of 450 units/ml of TNF as examined by bioassay. No basal production of TNF was observed in untreated cells. The treatment of cells with phorbol ester in the presence of all TNF-directed TFOs leads to the inhibition of production of TNF. TFOs directed to Herpes virus (B106-96) or other control TFOs (1208) had no effect on TNF production. The TFOs, at the concentration used, had no cytotoxic or cytostatic effects on THP-1 cells. Thus, the inhibition of TNF production by TFOs was specific and was not due to the nonspecific cellular toxicity. Among all the TNF-TFOs, J111-51 directed to the third intron of the TNF gene was found to be maximally effective giving 75% inhibition of TNF production at a concentration of 2 μM.

EXAMPLE 8

TNF is an Autocrine Growth Factor for Human Glioblastoma Cells

In order for a cytokine to act as an autocrine growth factor for a specific cell, the cell must: (1) produce that cytokine; (2) display receptors for that cytokine; and (3) proliferate in response to that cytokine. Furthermore, antibodies to that cytokine must inhibit the growth of the cytokine-producing cells. In order to demonstrate that TNF is an autocrine growth factor for glioblastoma tumor U-251 cells, the constitutive and phorbol ester-induced production of TNF from these cells was examined.

Figure 3:
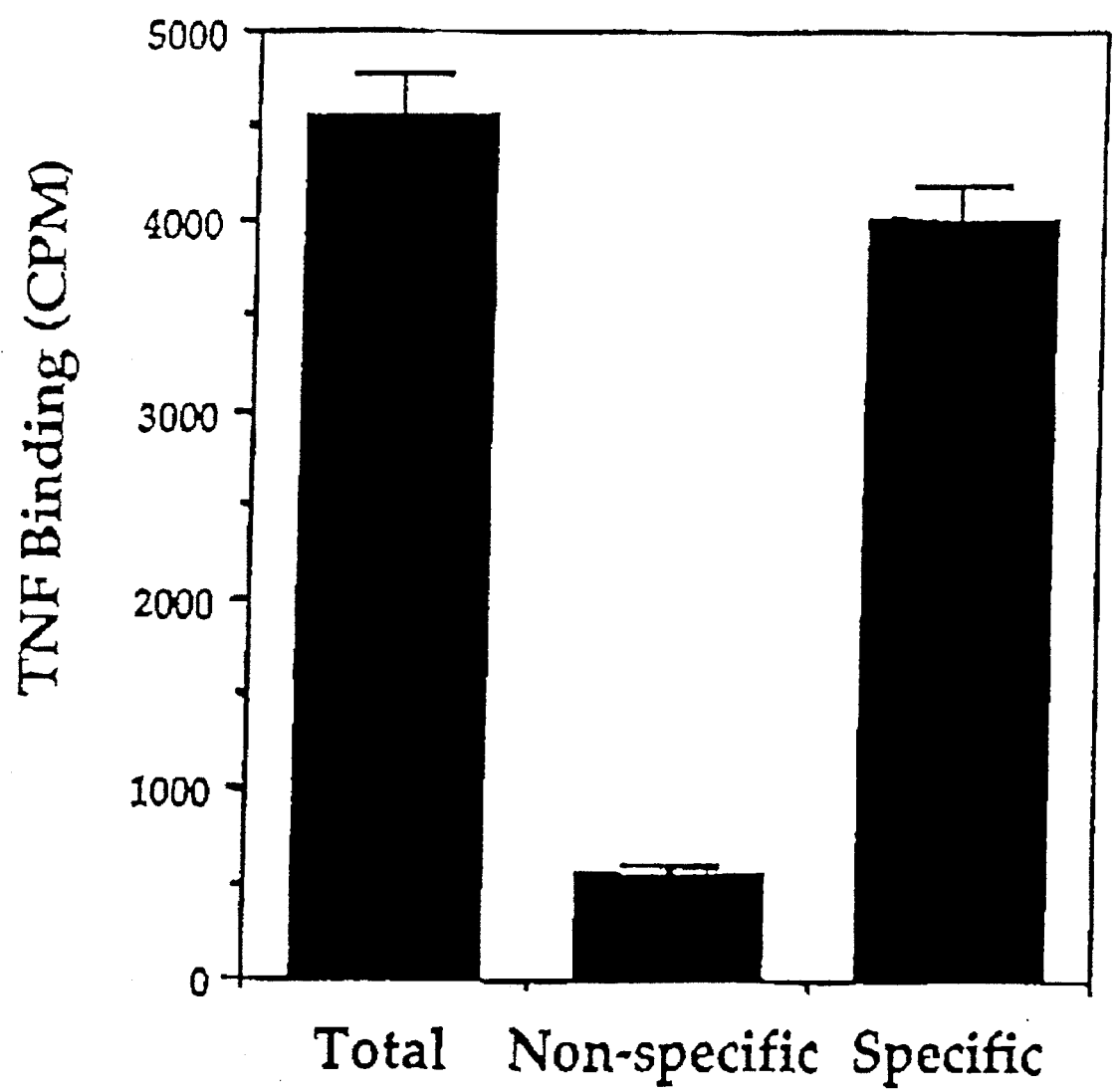
FIG. 3 shows the presence of TNF Receptor on the human glioblastoma (U-251) Cell Line.
Figure 4:
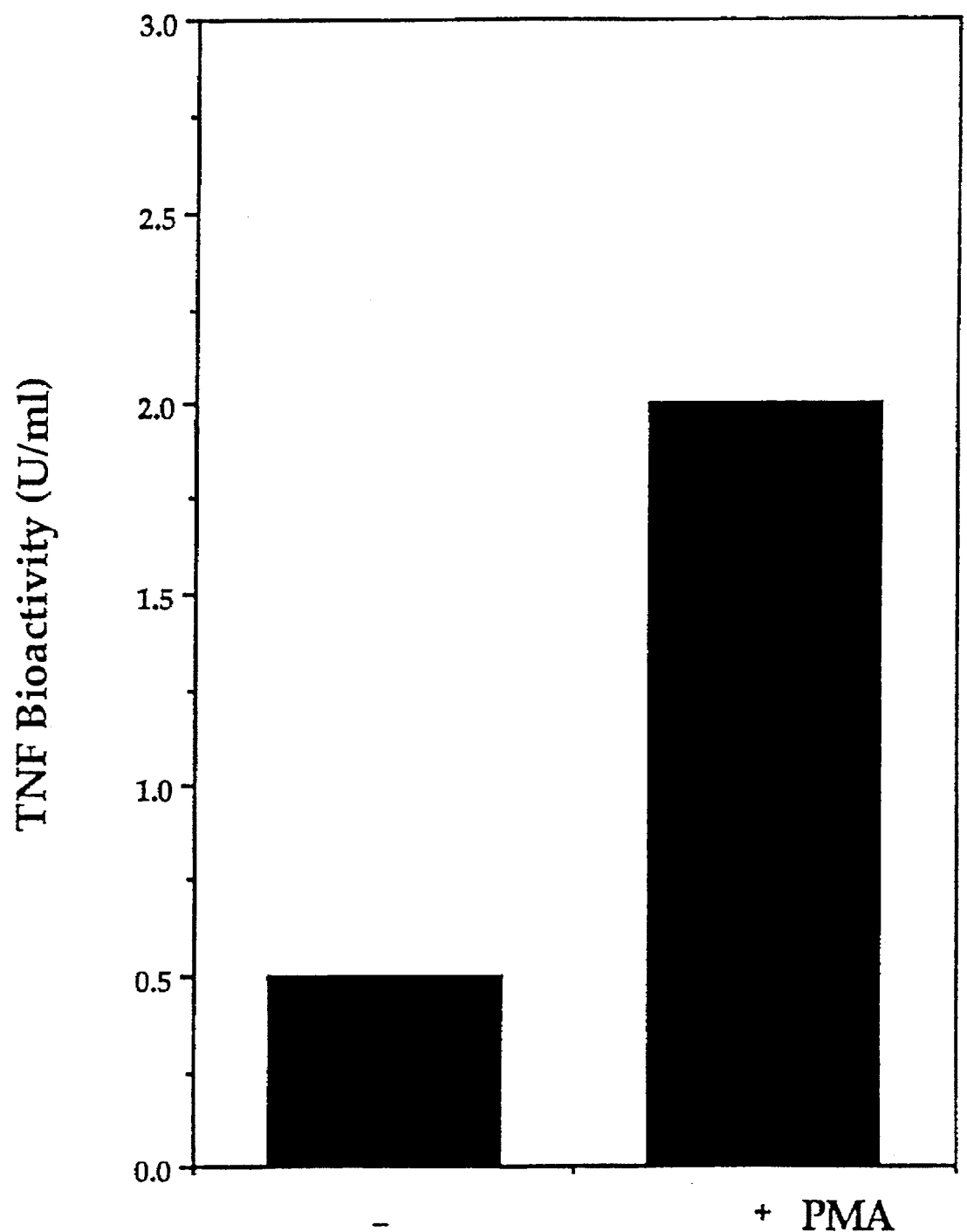
FIG. 4 shows the production of TNF by the human glioblastoma cell line, U-251. $1\times10^6$ cells (1 ml) in 12-well plates were incubated for 72 hours in the presence of PMA (100 ng/ml) at 37° C. Thereafter, the cell supernatants were harvested and assayed in triplicate for activity in L-929 bioassay for TNF.
Figure 5:
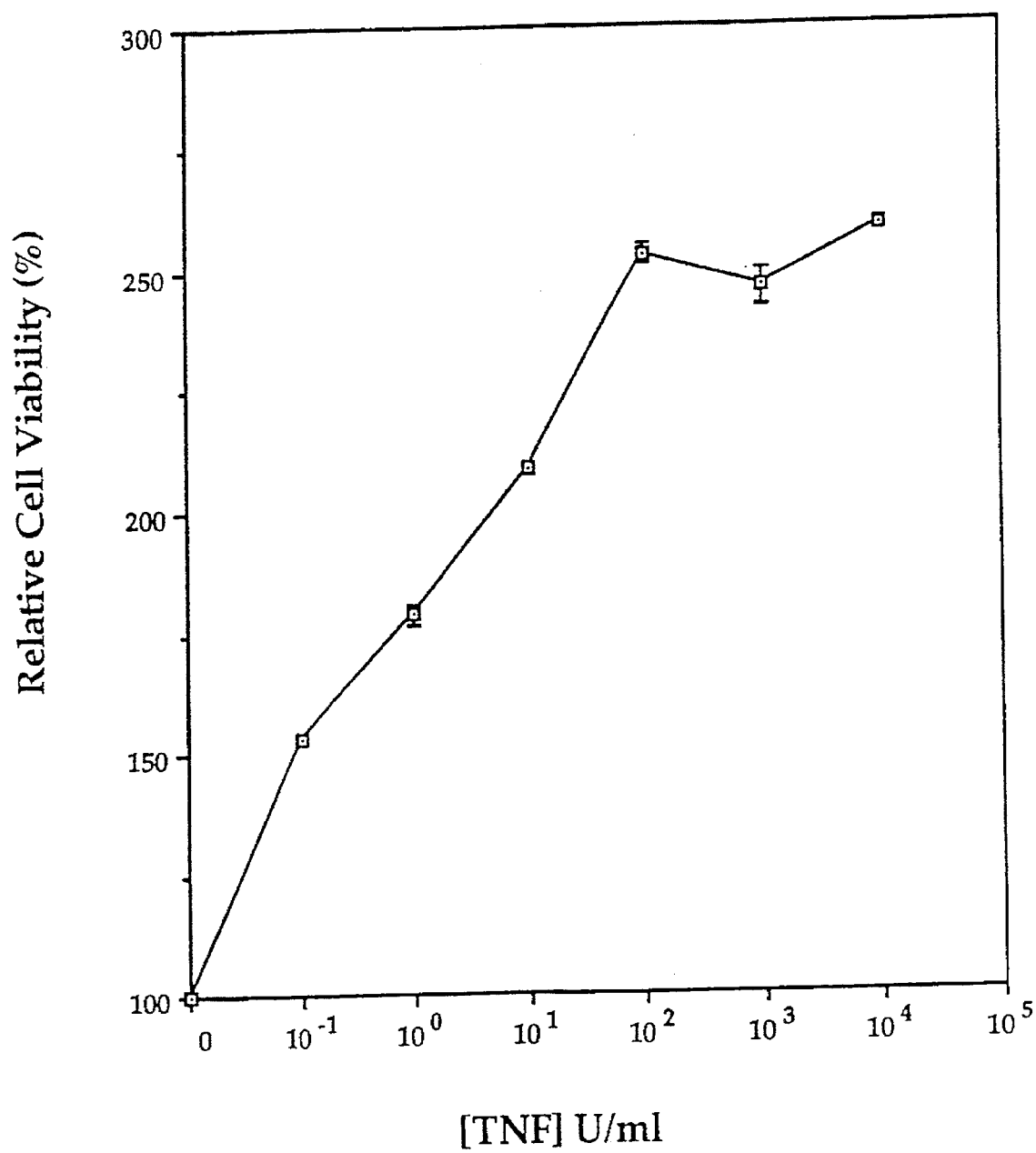
FIG. 5 shows the effect of TNF on the growth of human glioblastoma U-251 cells. Cells ($5\times10^3$ cells/0.1 ml/well) were plated overnight at 37° C., washed and then incubated with different concentrations of TNF for 72 hours. During last 24 hours of the incubation, 0.5 µCi tritiated thymidine was added, washed, harvested and monitored for the incorporation as indicated. All determinations were made in triplicate. The results are expressed as percentage of the control (untreated cells).
Figure 6:
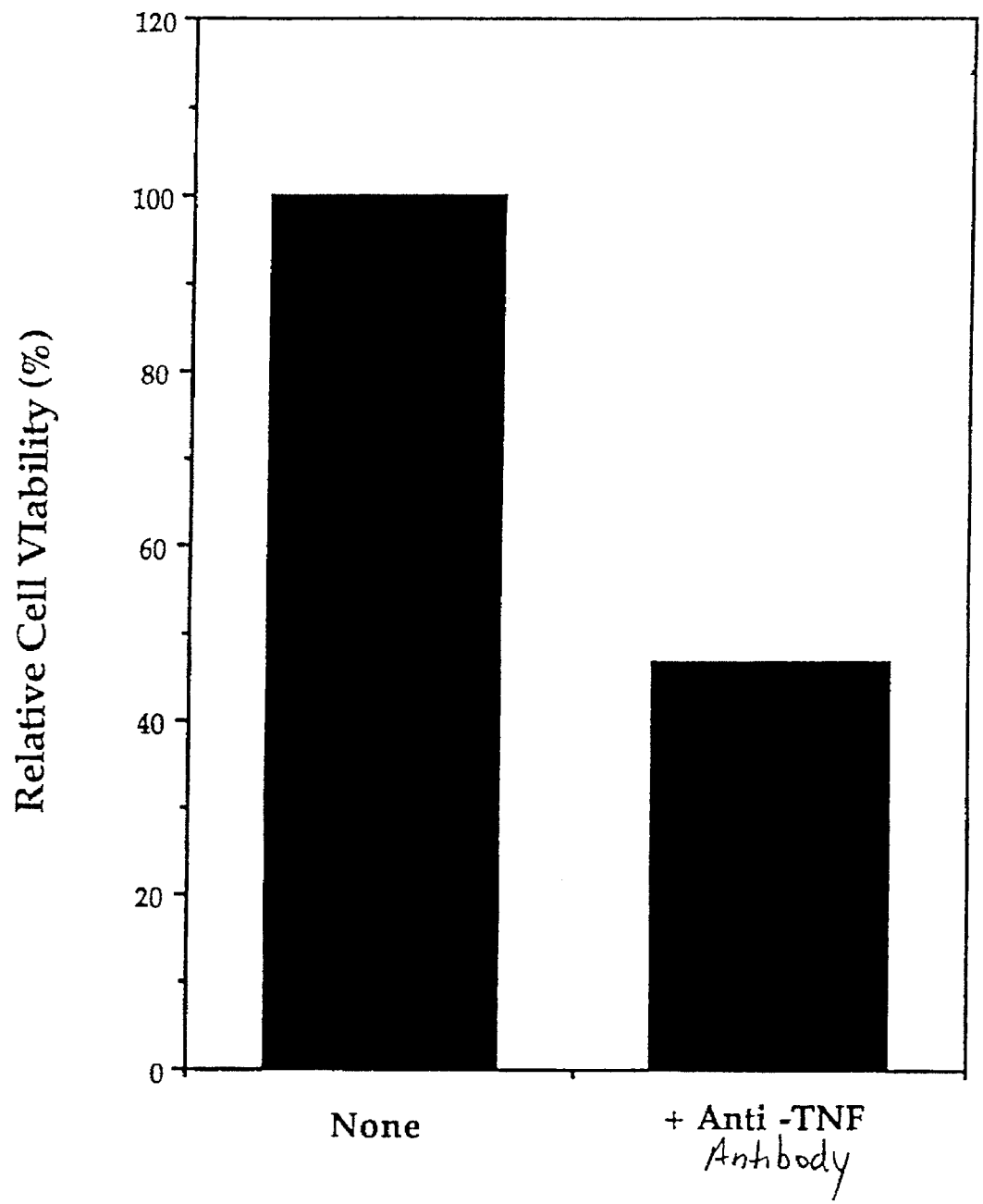
FIG. 6 shows the effect of an antibody to TNF on the growth of human glioblastoma U-251 cells. Cells ($5\times10^3$ cells/0.1 ml/well) were plated overnight at 37° C., washed and then incubated with antibodies to TNF for 72 hours. During last 24 hours of the incubation, 0.5 µCi tritiated thymidine was added, washed, harvested and monitored for the incorporation. All determinations were made in triplicate. The results were expressed as percentage of the control (untreated cells).

FIG. 3 shows the presence of TNF receptors on human gliobastoma (U-251) cell. FIG. 4 clearly indicates that U-251 cells produce low levels of TNF constituitively and its levels are elevated four-fold by treatment with phorbol ester. In addition, TNF acts as a growth factor for U-251 cells. FIG. 5 illustrates that TNF enhances the proliferation of these cells in a dose dependent manner. Approximately two to three-fold stimulation in cell growth was observed with 100 units/ml of TNF. TNF-neutralizing monoclonal antibodies also inhibit the proliferation of U-251 cells. FIG. 6 shows that antibodies sufficient to neutralize 4 units/ml of TNF bioactivity inhibited approximately 60% growth of the cells within 3 days. Thus, TNF is an autocrine growth factor for U-251 glioblastoma cells.

EXAMPLE 9

TNF-TFO Inhibits the Proliferation of Glioblastoma Tumor Cells

Figure 7:
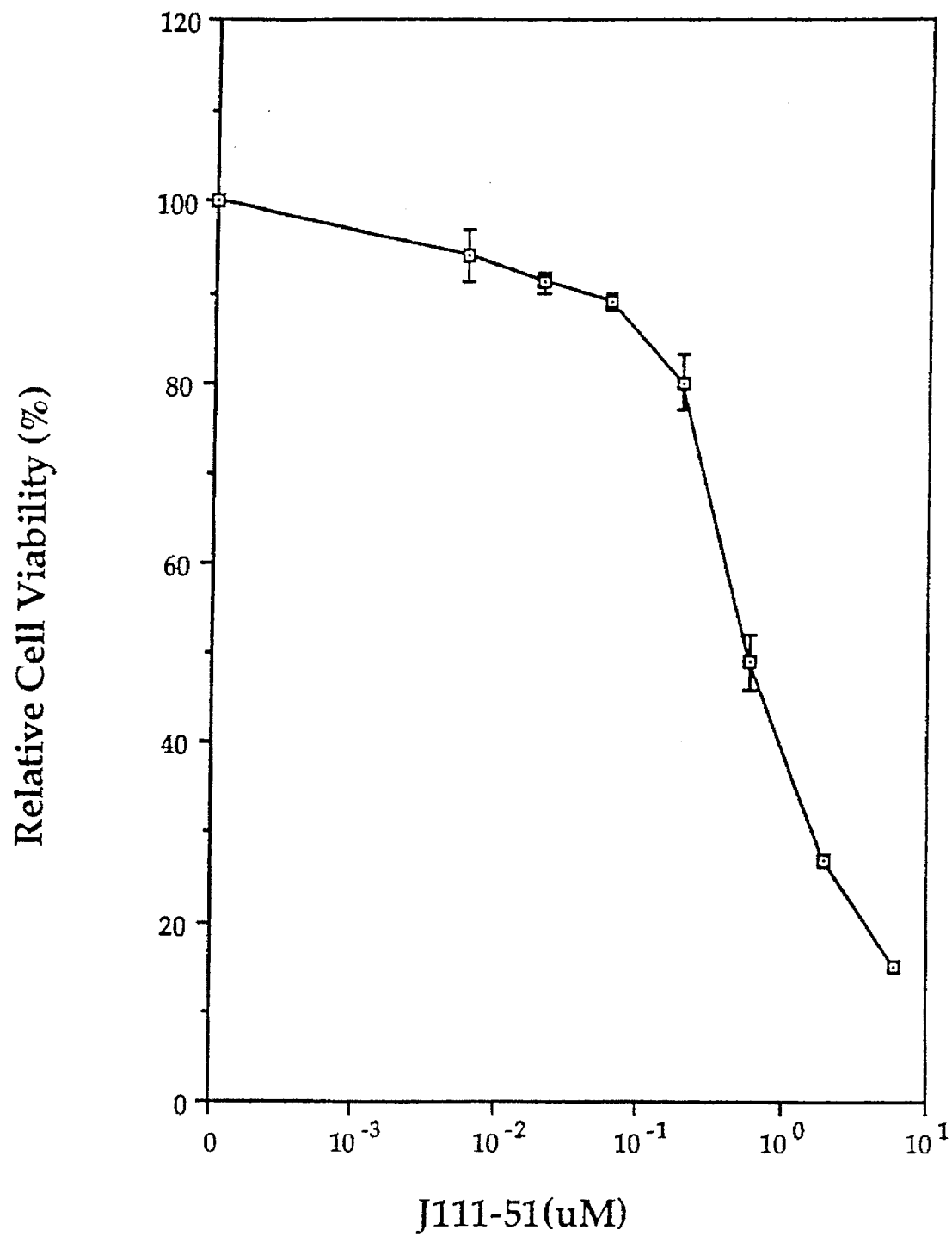
FIG. 7 shows the effect of the TNF-TFO (J111-51) on the growth of human glioblastoma U-251 Cells. Cells (5×10³ cells/0.1 ml/well) were plated overnight at 37° C., washed and then incubated with different concentrations of TNF-TFO for 72 hours. During the last 24 hours of the incubation, 0.5 μCi tritiated thymidine was added, washed, harvested and monitored for the incorporation. All determinations were made in triplicate. The results are expressed as percentage of the control (untreated cells).

Since a TNF-TFO specifically blocked TNF production and also since TNF is an autocrine growth factor for glioblastoma tumor cells, the effect of TFOs on the proliferation of U-251 cells was examined. Among all the TNF-TFOs, J111-51 was examined because of its ability to maximally inhibit TNF production. FIG. 7 clearly illustrates that a 1 μM concentration of TFO inhibited approximately 80% of cell growth. This effect was dose-dependent and increased to 90% inhibition when the concentration of J111-51 was raised to 6 μM.

EXAMPLE 10

Antiproliferative effects of J111-50 and J111-51

Figure 8A:
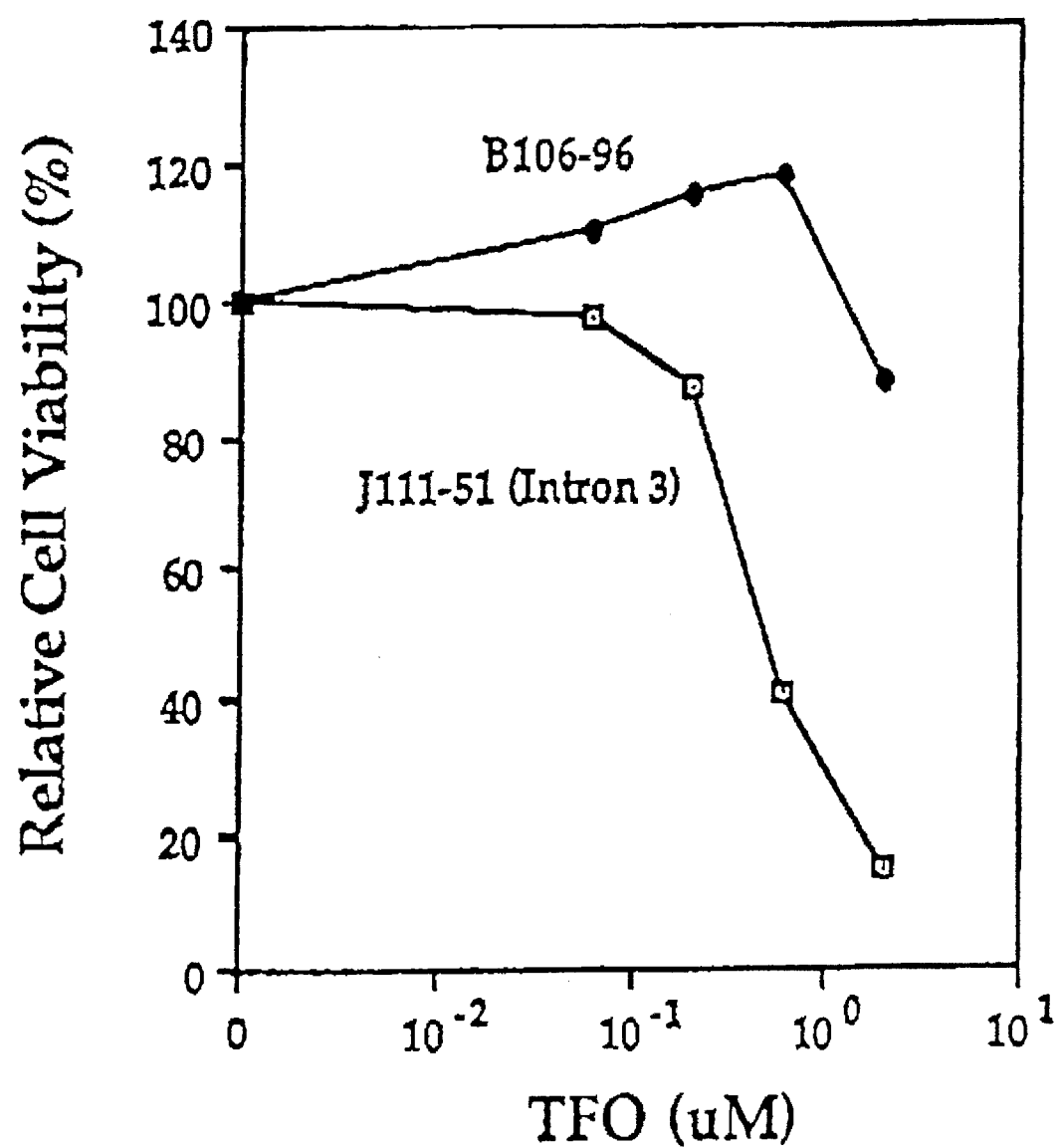
FIG. 8 shows the antiproliferative effects of the TFOs J111-51 (Intron 3) and J111-50 (Intron 3) on a human glioblastoma (U-251) cell line.
Figure 8B:
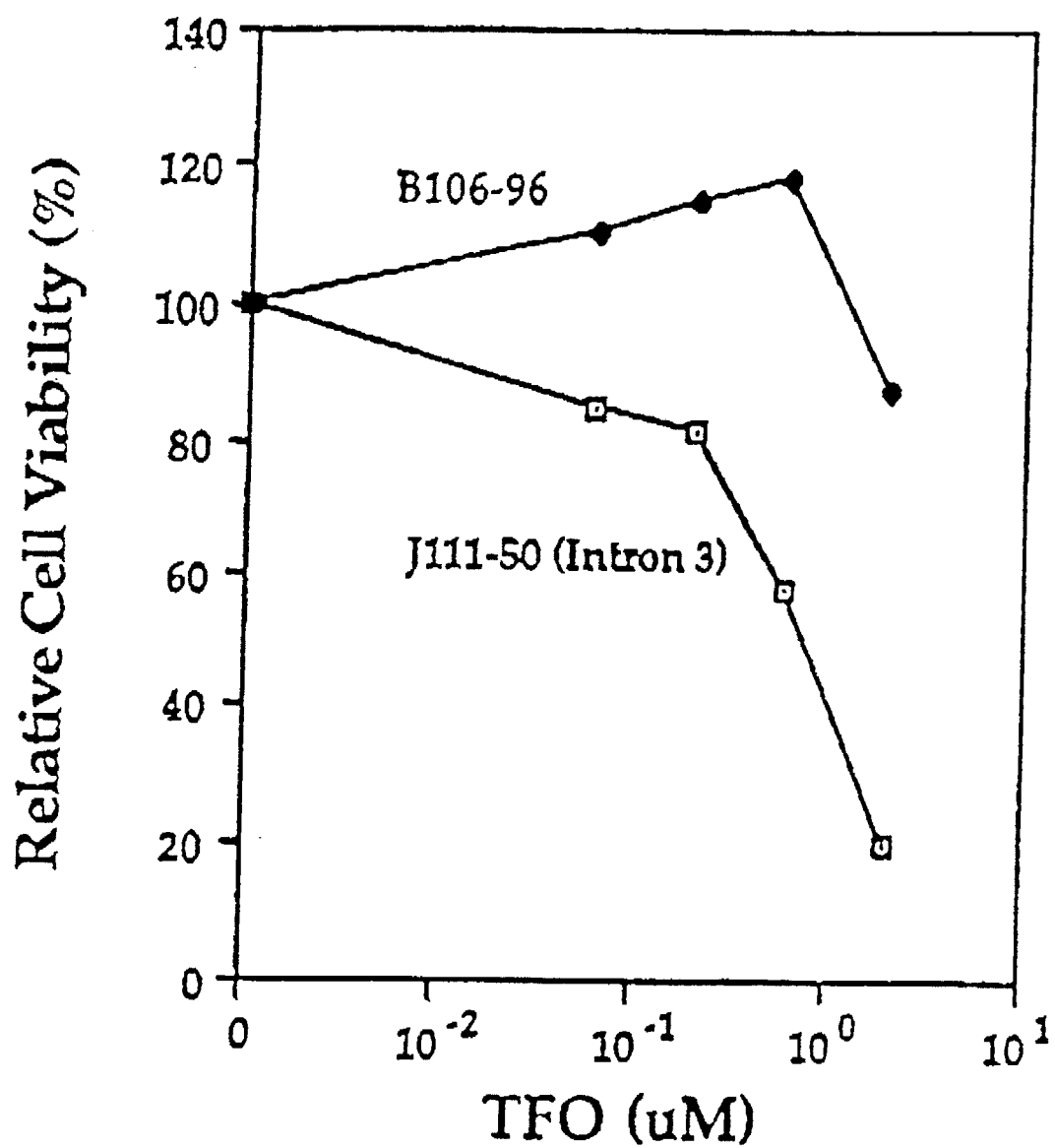
Figure 14:
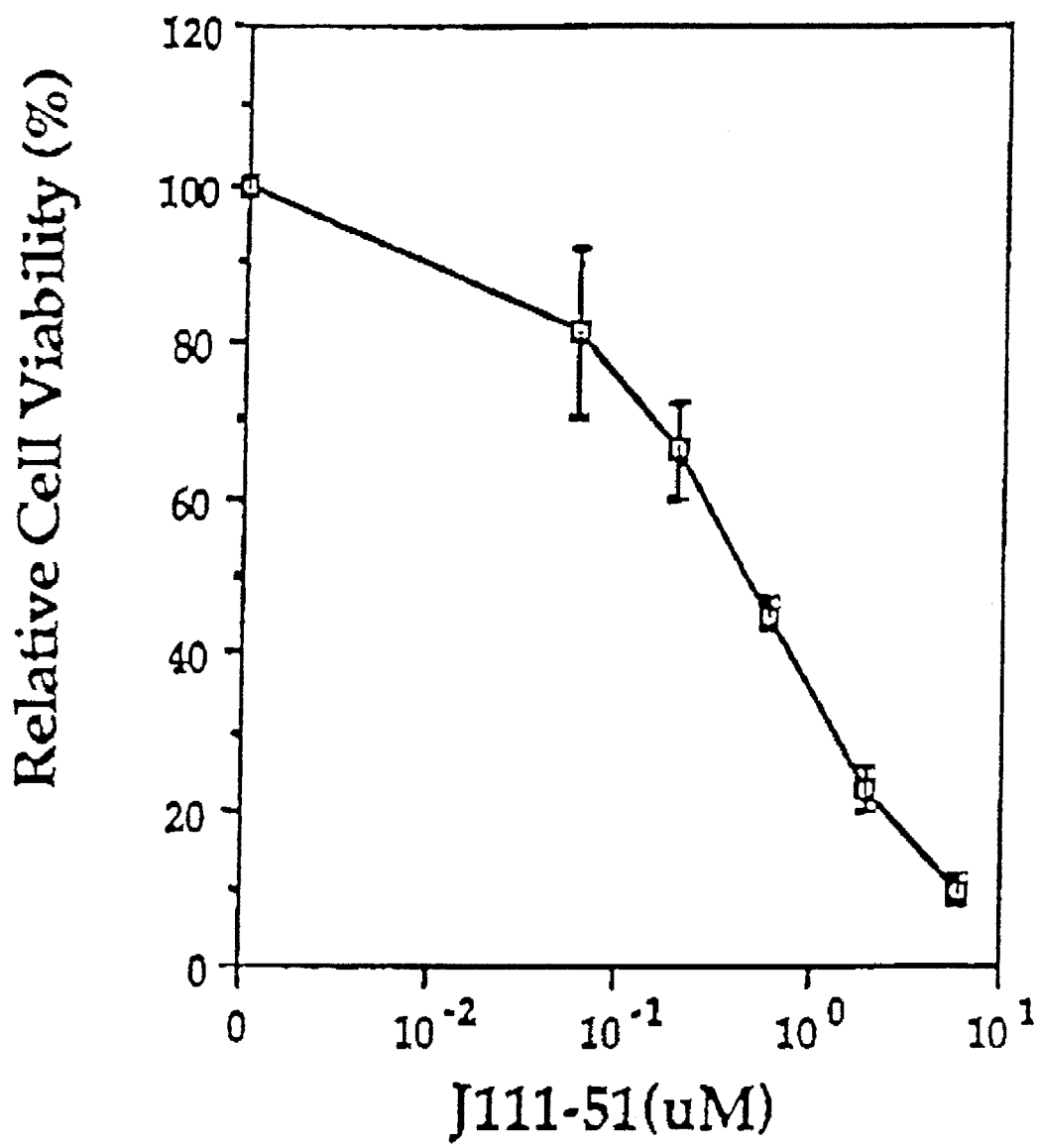
FIG. 14 shows the antiproliferative effects of TFO J111-51 (Intron 3) on a human glioblastoma UWR-1 cell line.

FIGS. 8, top and bottom the antiproliferative effects of the TFOs J111-51 (Intron 3) and J111-50 (Intron 3) on a human glioblastoma (U-251) cell line, respectively. Both J111-51 and J111-50 inhibit U-251 cell growth by approximately 80% at about 1 μM. In contrast, the control oligonucleotide B106-96 had virtually no effect. The TFO J111-51 had a similar antiproliferative effect on the human glioblastoma UWR-1 cell line. As shown in FIG. 14, the TFO J111-51 inhibited the growth of UWR-1 cells by about 75% at about 1 μM.

EXAMPLE 11

Antiproliferative effects of J111-50 and J109-50

Figure 9A:
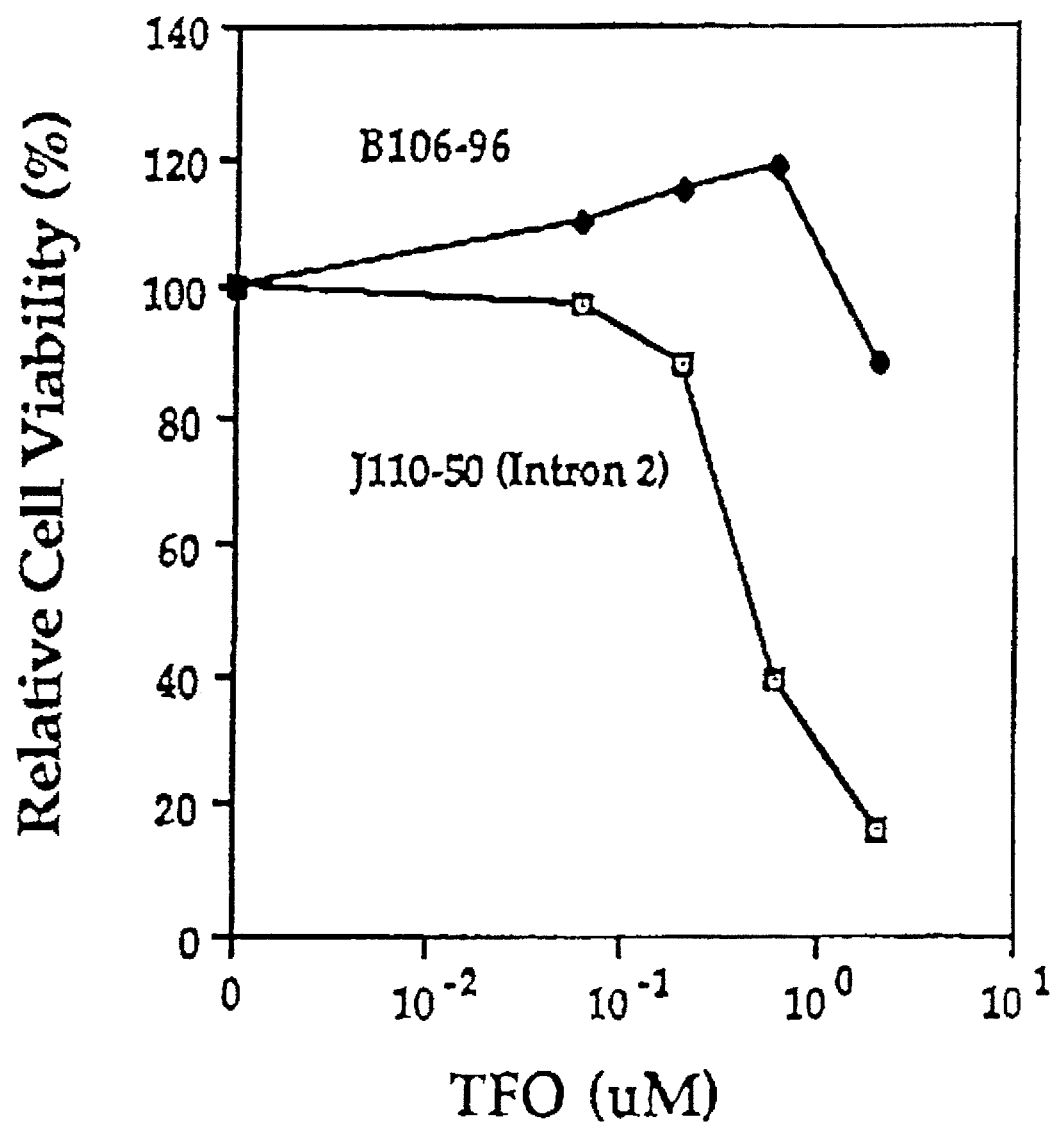
FIG. 9 shows the antiproliferative effects of the TFOs J111-50 (Intron 3) and J109-50 (NF-kB) on a human glioblastoma (U-251) cell line.
Figure 9B:
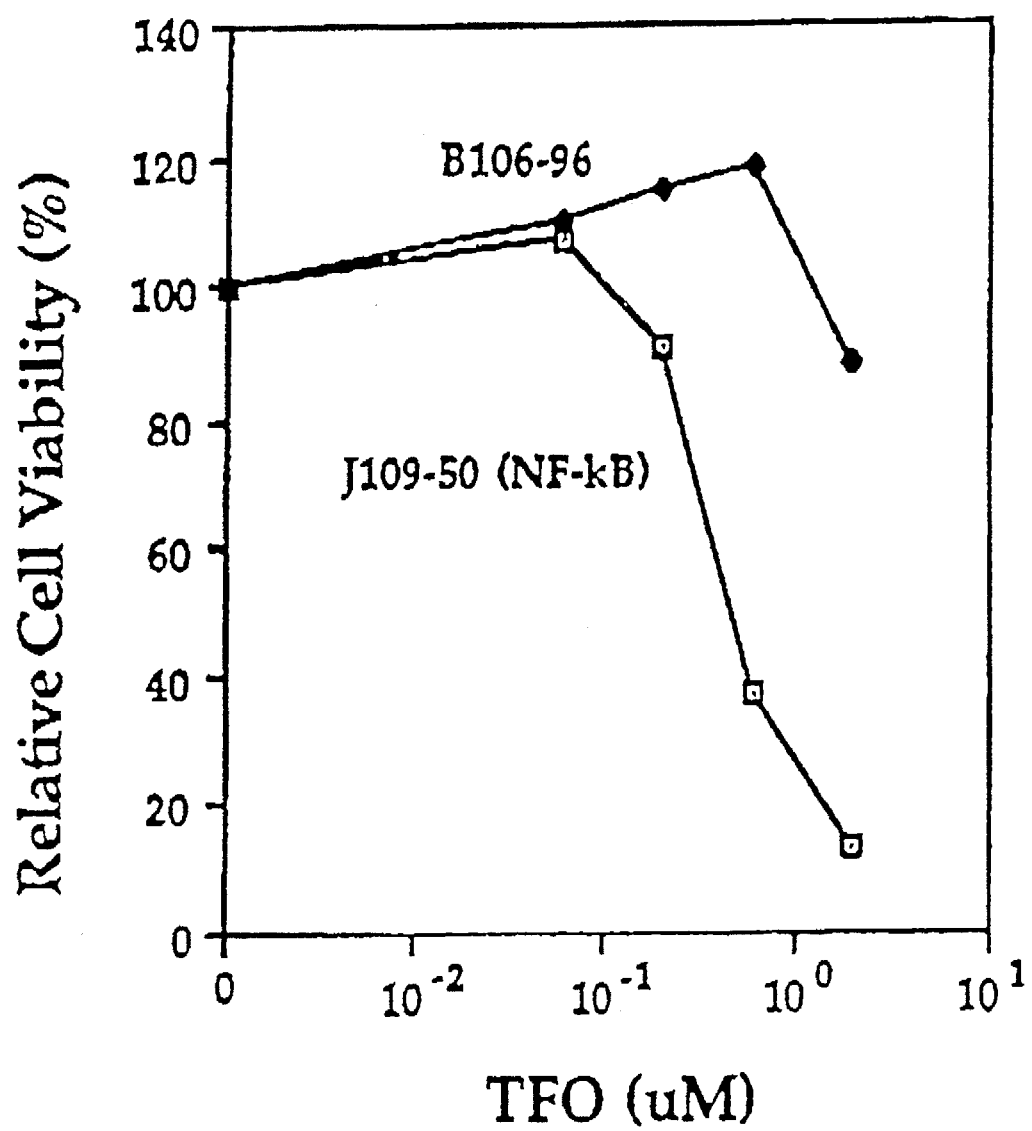

FIGS. 9, top and bottom the antiproliferative effects of the TFOs J111-50 (Intron 3) and J109-50 (NF-kB) on a human glioblastoma (U-251) cell line, respectively. Both J111-50 (directed to Intron 3) and J109-50 (directed to NF-kB) inhibited the growth of U-251 cells by about 80% at approximately 1 μM.

EXAMPLE 12

Antiproliferative effect of J108-57

Figure 10:
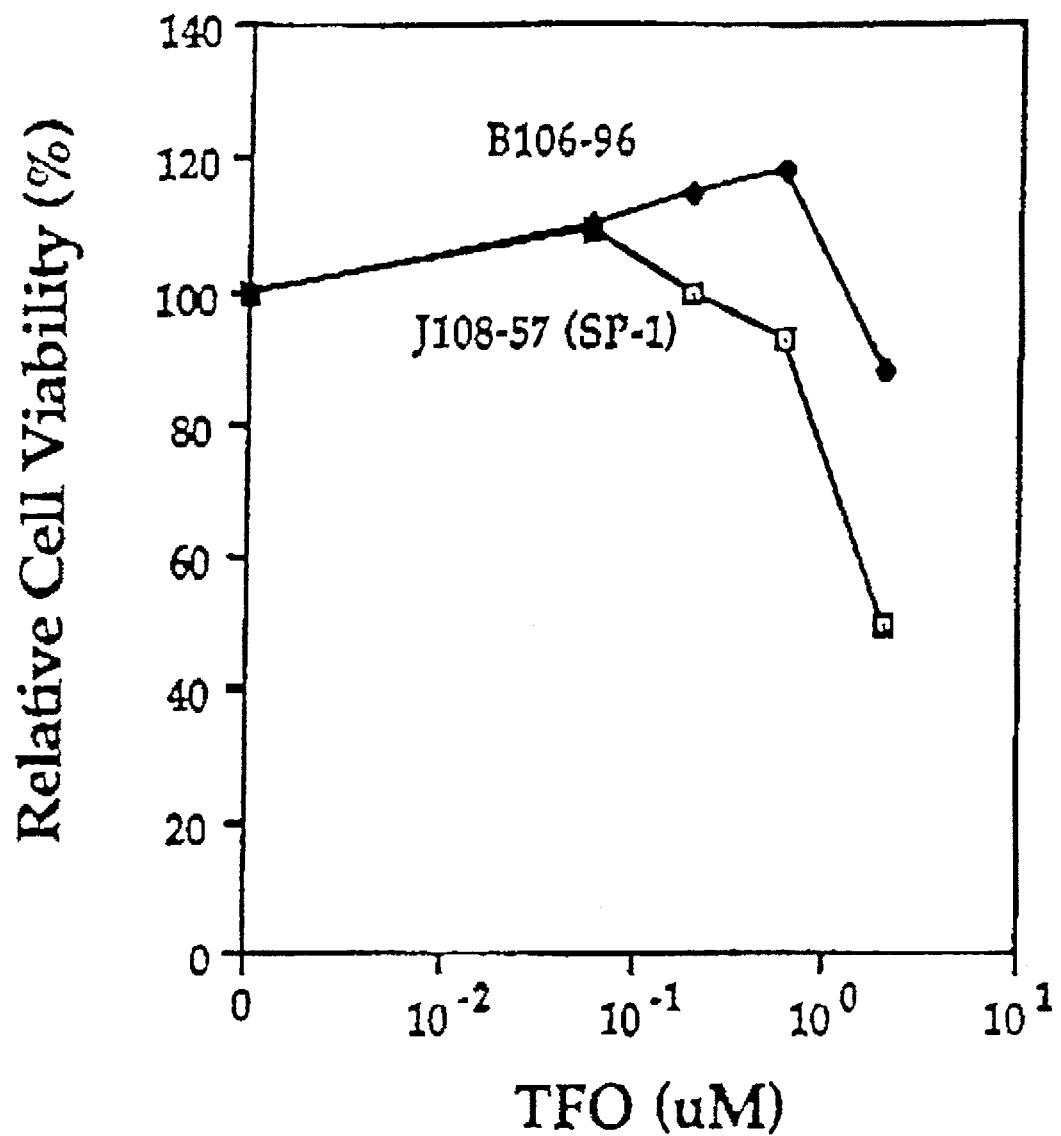
FIG. 10 shows the antiproliferative effects of the TFO J108-57 (SP-1) on a human glioblastoma (U-251) cell line.

FIG. 10 shows the antiproliferative effect of J108-57 on U-251 cells. The TFO J108-57 inhibited the growth of U-251 cells by approximately 45% at 1 μM.

EXAMPLE 13

Antiproliferative effect of an anti-TNF antibody on R4 cells

Figure 11:
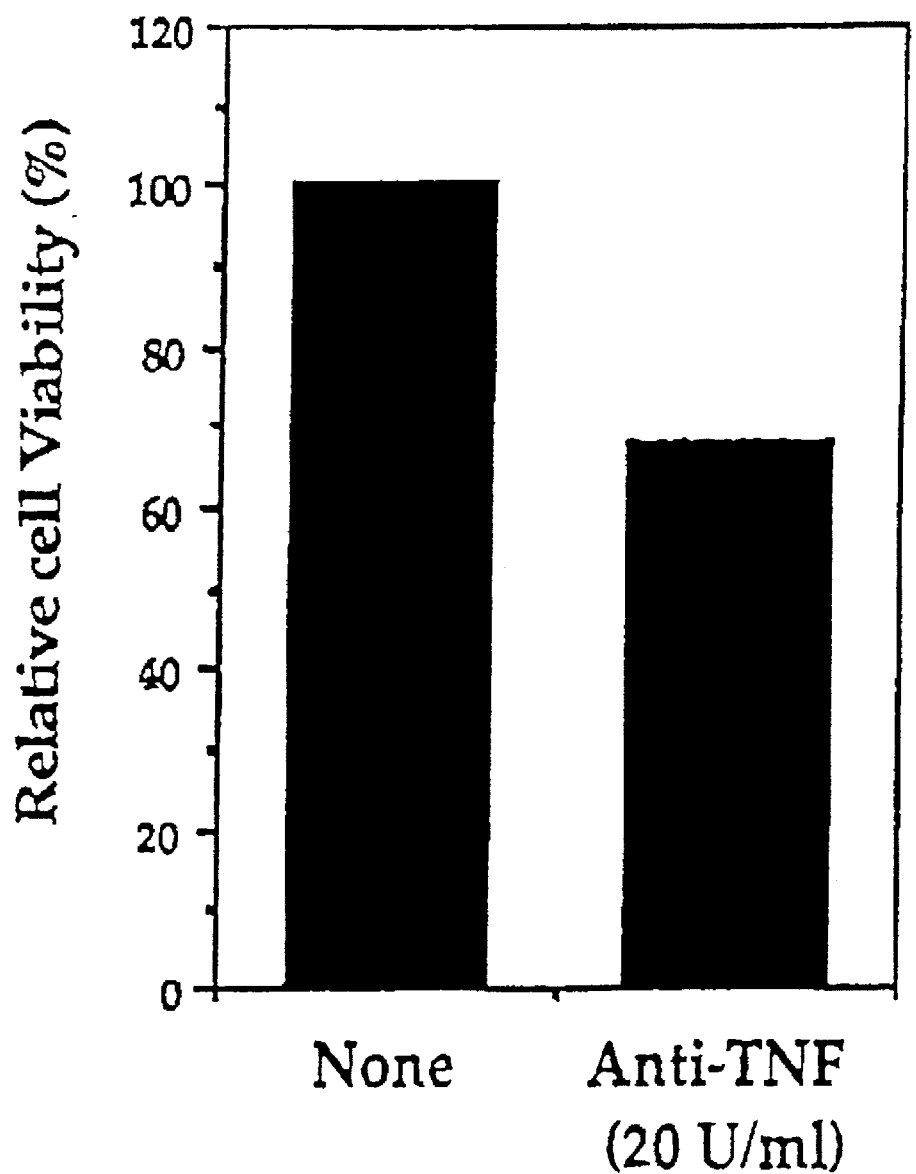
FIG. 11 shows the growth inhibition of the human renal carcinoma cell lines (R-4) by a monoclonal Anti-TNF antibody.
Figure 12:
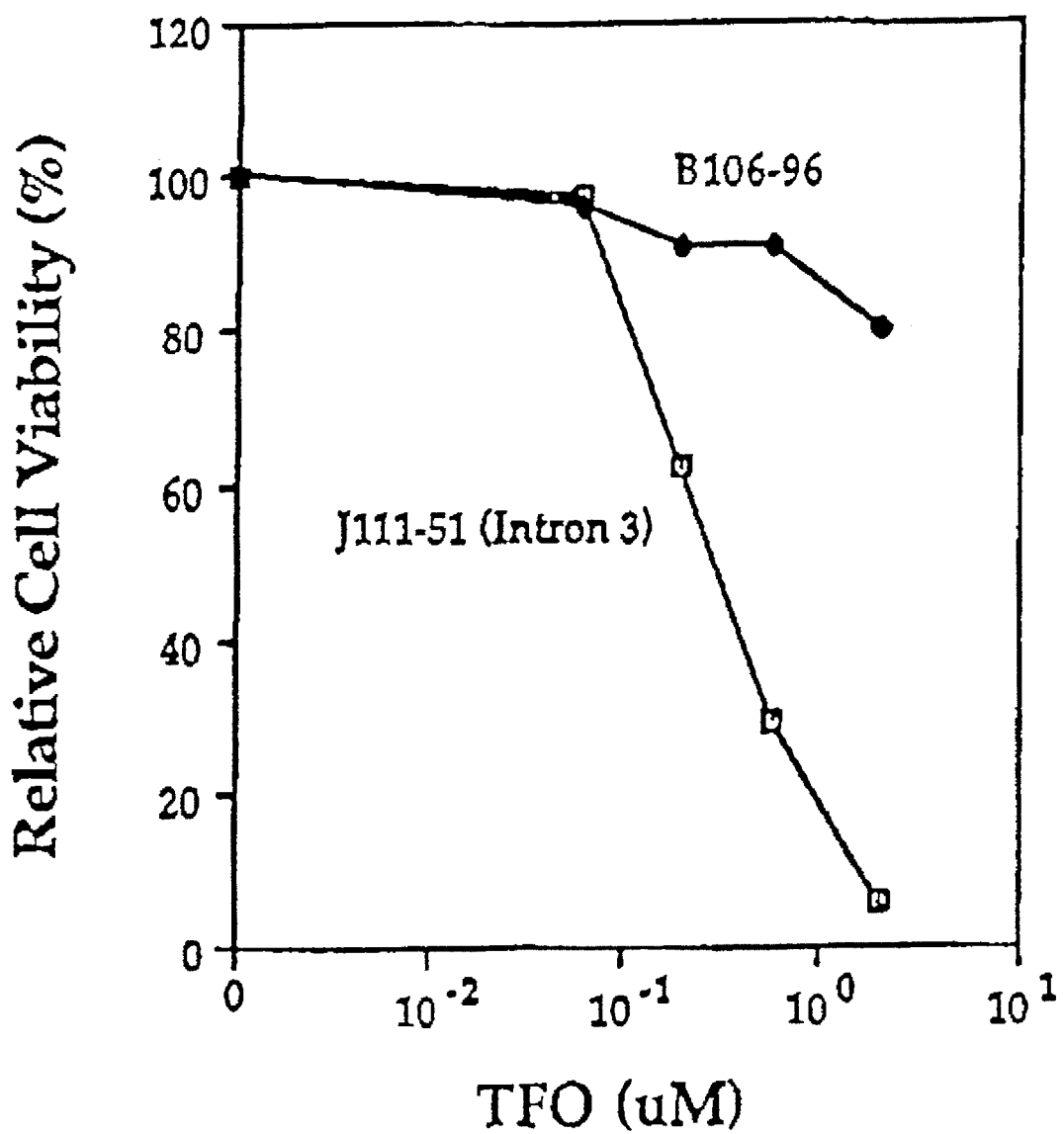
FIG. 12 shows a comparison of the antiproliferative effects of the TFOs-J111-51 (Intron 3) and B106-96 on a human renal carcinoma (R-4) cell line.
Figure 13:
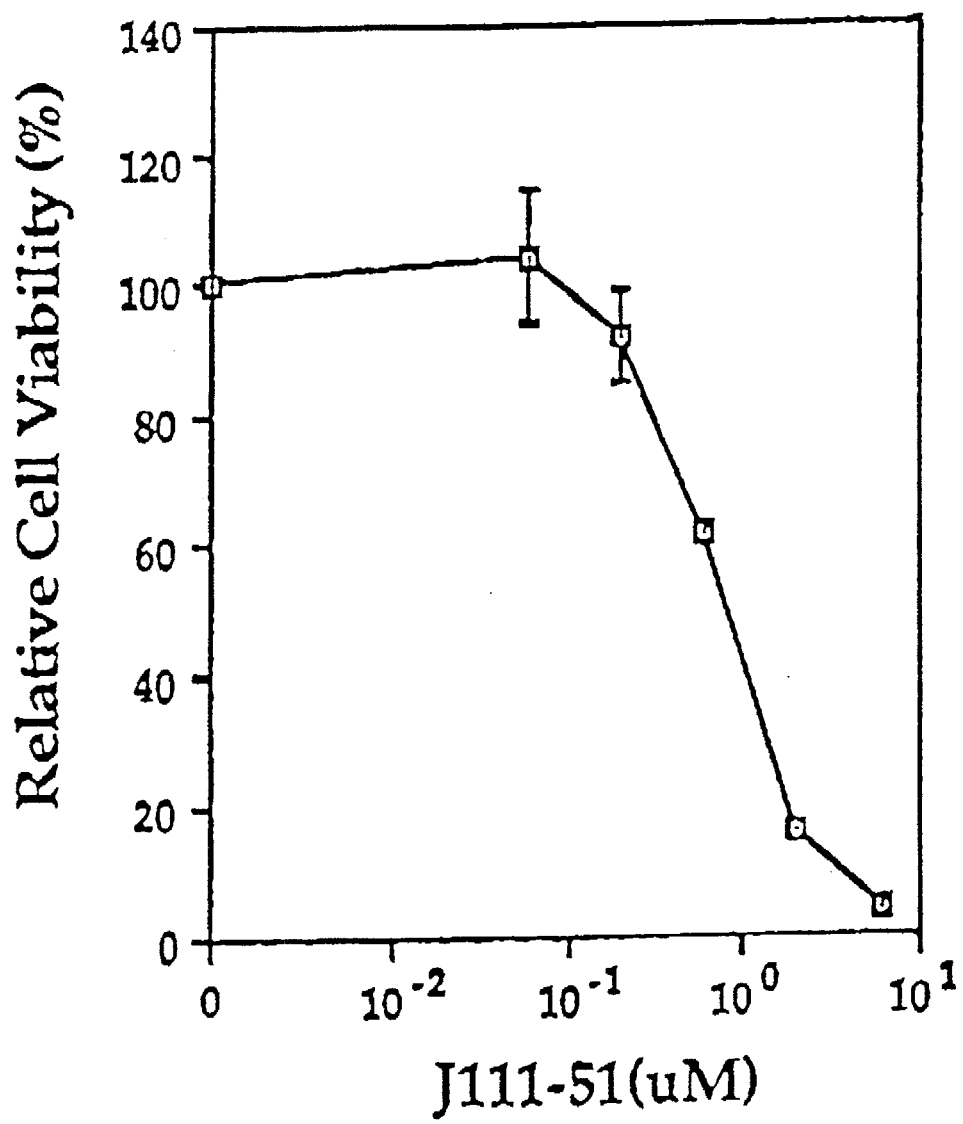
FIG. 13 shows the antiproliferative effects of TFO J111-51 (Intron 3) on a human renal carcinoma R-4 cell line.

FIG. 11 shows that an anti-TNF antibody inhibited the growth of the human renal carcinoma cell line, R-4, by about 35% at a dose of 20 U/ml. Furthermore, as shown in FIGS. 12 and 13, the TFO, J111-51, inhibited the growth of R-4 cells by more than 95% at a dose of about 1 μM. In contrast, the control TFO, B106-96 had virtually no effect (FIG. 12).

EXAMPLE 14

Triple helix basis for TFO effects

FIG. 14 shows that the antiproliferative effects of triplex forming oligonucleotides is due to the formation of triple helices. That is, FIG. 14 shows that the oligonucleotide J111-56 (a scrambled sequence of TFO J111 -51) and oligonucleotide J111-01 (the reverse sequence of J111-51) are far less effective in inhibiting U-251 cells than J111-51.

Table II shows the synergistic antiproliferative effects of different TFOs on the human glioblastoma (U251) cell line. To demonstrate the synergistic antiproliferative effects seen in Table II, 5×10$^3$ cells were plated overnight at 37° C. and then incubated with TFO (0.2 μM). After 48 hours at 37° C., cells were pulsed with thymidine for 24 hours prior to harvesting. The thymidine incorporation by untreated cells was expressed as 100%. All determinations were made in triplicate. TFO 109-50, 111-51, 108-56 and 108-57 are from NF-kB (−237 to −208); Intron 3 (+1429 to +1456); and SP-1 (−58 to −33) sites respectively. J109-50 had amino group whereas others were had cholesterol modification at 3' end. The TFOs B106-96 and 1206 had phosphorothioate backbone.

TABLE II

Synergistic Antiproliferative Effects of TFOs on U-251 Cells

| TFO | Relative Cell Viability (%) |
| --- | --- |
| None | 100 |
| J109-50 | 52 |
| J111-51 | 44 |
| J108-56 | 94 |
| J108-57 | 55 |
| J109-50 + J111-51 | 30 |
| J109-50 + J108-56 | 48 |
| J109-50 + J108-57 | 47 |
| J111-51 + J108-56 | 43 |
| J111-51 + J108-57 | 33 |
| J109-50 + J111-51 + J108-56 | 32 |
| J109-50 + J111-51 + J108-57 | 25 |
| B106-96 | 99 |
| 1208 | ND |

In the present invention, the effect of synthetic oligodeoxyribonucleotides directed to the TNF gene on the production of TNF and on the growth of TNF-dependent tumors cells was seen. Triple helix forming oligonucleotides specific to the TNF gene inhibited the production of TNF from activated macrophages whereas control TFOs were ineffective. Among all the TFOs, maximum inhibition of TNF production was observed with TFO directed to the third intron in the TNF gene. In glioblastoma tumors in which TNF acts as an autocrine growth factor, TNF-TFO inhibits the growth of these cells.

TNF is an autocrine growth factor for number of different type of tumors including breast adenocarcinoma, ovarian carcinoma, glioblastoma and different types of leukemia. The present invention involves the inhibition of growth of these tumors by interrupting an autocrine loop by TFOs.

TNF is a highly pleiotropic cytokine. Besides tumorigenesis, its role in promoting the replication of human immunodeficiency virus (HIV-1), in mediating septic shock, cachexia, in graft vs host disease (e.g; bone morrow transplantation), in mediation of autoimmune disease (e.g; arthritis), cerebral malaria and fever is well established. The ability of the TFOs of the present invention to block TNF production has therapeutic value in these various disease states.

All patent and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The triplex forming oligonucleotides, methods, procedures and techniques described herein are presently representative of preferred embodiments, are intended to be exemplary and are not intended as limitations on the scope of the present invention. Changes therein and other uses will occur to those skilled in the art which are encompassed within the spirit of the invention or defined by the scope of the appended claims.

We claim:

1. A method for killing a neoplastic cell requiring production of tumor necrosis factor-α for viability comprising the step of contacting said cell in vitro with an amount of triplex forming oligonucleotide selected from the group consisting of J109-50 (SEQ ID NO:1), J108-57 (SEQ ID NO:3), and J111-51 (SEQ ID NO.2), which is sufficient to inhibit the transcription of the gene encoding tumor necrosis factor alpha in said cell and kill said cell.

2. The method of claim 1, wherein said neoplastic cell is a human glioblastoma cell.

3. The method of claim 1, wherein said neoplastic cell is a human renal carcinoma cell.

4. A triplex forming oligonucleotide selected from the group J109-50 (SEQ. ID No. 1), J108-57 (SEQ. ID No.3), and J111-51 (SEQ. ID No. 2).

* * * * *

UNITED STATES PATENT AND TRADEMARK OFFICE
CERTIFICATE OF CORRECTION

PATENT NO. : 5,650,316               Page 1 of 4
DATED      : Jul. 22, 1997
INVENTOR(S) : Bharat B. Aggarwal, et al It is certified that error appears in the above-identified patent and that said Letters Patent is hereby corrected as shown below:

In Column 1, line 22, "has" should read --have--.

In Column 1, line 23, please insert the word --the-- between the words "for" and "last".

In Column 1, line 46, "type" should read --types--.

In Column 1, line 48, "type" should read --types--.

In Column 2, lines 53-54, please insert the word --the-- between the words "During" and "last".

In Column 2, line 63, please insert the word --the-- between the words "During" and "last".

Column 3, line 23, "TFOs-J111-51" should read --TFO J111-51--.

In Column 4, line 20, "+1429- to" should read --+1429 to--.

In Column 4, line 23, "order-to" should read --order to--.

In Column 4, approximately line 38, the fourth line under the heading "Gene Target" in TABLE I, please insert a --)-- at the end of the line to complete the parenthesis.

UNITED STATES PATENT AND TRADEMARK OFFICE
CERTIFICATE OF CORRECTION

PATENT NO. : 5,650,316
DATED : Jul. 22, 1997
INVENTOR(S) : Bharat B. Aggarwal, et al It is certified that error appears in the above-identified patent and that said Letters Patent is hereby corrected as shown below:

In Column 4, lines 57-58, please insert the word --are-- between the words "TNF" and "useful".

In Column 5, line 22, please insert a comma after the words "autoimmune diseases".

In Column 5, line 26, "examples-of" should read --examples of--.

In Column 5, line 64, "Mass" should read --MA--.

In Column 6, line 18, "µg mole" should read --µmole--.

In Column 6, line 57, please insert the word --a-- between the words "as" and "nonspecific".

In Column 7, line 44, please insert the word --a-- between the words' "and" and "test".

In Column 8, line 3, "TNF-a" should read --TNF-α--.

In Column 8, line 4, "TNF-a" should read --TNF-α--.

In Column 8, line 9, "TNF-a" should read --TNF-α--.

In Column 8, lines 50-51, "constitutive" should read --constituitive--.

In Column 8, line 55, "cell" should read --cells--.

In Column 9, line 18, "FIGS. 8" should read --FIG. 8--.

UNITED STATES PATENT AND TRADEMARK OFFICE
CERTIFICATE OF CORRECTION

PATENT NO. : 5,650,316    Page 3 of 4
DATED : Jul. 22, 1997
INVENTOR(S) : Bharat B. Aggarwal, et al It is certified that error appears in the above-identified patent and that said Letters Patent is hereby corrected as shown below:

In Column 9, line 18, please insert the words --panels show-- between the words "bottom" and "the".

In Column 9, line 32, "FIGS. 9" should read --FIG. 9--.

In Column 9, line 32, please insert the words --panels show-- between the words "bottom" and "the".

In Column 10, line 8, please delete the word --were-- between the words "others" and "had".

In Column 10, line 8, please insert the word --the-- between the words "at" and "3'".

In Column 10, line 31, "tumors" should read --tumor--.

In Column 10, line 41, please insert the word --a-- between the words "for" and "number".

In Column 10, line 42, "type" should read --types--.

UNITED STATES PATENT AND TRADEMARK OFFICE
CERTIFICATE OF CORRECTION

PATENT NO. : 5,650,316

DATED : Jul. 22, 1997

INVENTOR(S) : Bharat B. Aggarwal, et al

It is certified that error appears in the above-identified patent and that said Letters Patent is hereby corrected as shown below:

In Column 10, line 55, "patent" should read --patents--.

Signed and Sealed this

Third Day of November, 1998

*Attest:*

BRUCE LEHMAN

*Attesting Officer*   Commissioner of Patents and Trademarks